United States Patent [19]

Keefer et al.

[11] Patent Number: 4,535,154

[45] Date of Patent: Aug. 13, 1985

[54] REDUCTIVE DESTRUCTION OF NITROSAMINES, HYDRAZINES, NITRAMINES, AZO- AND AZOXY-COMPOUNDS

[75] Inventors: Larry K. Keefer, Bethesda; George Lunn, Frederick, both of Md.

[73] Assignee: United States of America, Washington, D.C.

[21] Appl. No.: 513,249

[22] Filed: Jul. 13, 1983

Related U.S. Application Data

[63] Continuation of Ser. No. 282,844, Jul. 13, 1981, abandoned.

[51] Int. Cl.$^3$ .................. C07D 295/00; C07C 85/11
[52] U.S. Cl. .................. 544/106; 564/112; 564/113; 564/415; 564/416; 564/417; 564/418; 564/414; 564/422; 564/448; 564/489; 564/494; 544/358; 546/184; 548/400
[58] Field of Search ............ 564/112, 113, 415, 416, 564/465, 489, 494, 414, 417, 418, 422, 448; 544/106, 358; 546/184; 548/400

[56] References Cited

U.S. PATENT DOCUMENTS

| | | | |
|---|---|---|---|
| 2,754,329 | 7/1956 | Bashford | 564/113 |
| 2,979,505 | 4/1961 | Tuemmler et al. | 564/465 |
| 3,187,051 | 6/1965 | Mock | 564/465 |
| 3,305,585 | 2/1967 | Besson et al. | 564/465 |
| 3,499,931 | 3/1970 | Tindall | 564/489 X |
| 4,038,321 | 7/1977 | Thatcher et al. | 564/113 X |

OTHER PUBLICATIONS

Grillot, G. F., "Journal of American Chemical Society", vol. 66, p. 2124 (1944).
Paal, C. & Yao, W., "Berichte", Jahrg. 63, pp. 57–66, (1930).
Smith, "Open Chain Nitrogen Compounds", pp. 478–479 (1966).
Fieser et al., "Reagents for Organic Synthesis", vol. I, pp. 718–720 (1967).
Sidgewicks, "Organic Chemistry of Nitrogen", 3rd Ed., pp. 593–595 (1966).
Seebach, D. & Wykypiel, W., "Synthesis", pp. 423–424 (1979).

*Primary Examiner*—Anton H. Sutto
*Assistant Examiner*—John A. Sopp
*Attorney, Agent, or Firm*—Spencer & Frank

[57] ABSTRACT

A method for the reduction of nitrogen compounds containing an N—N or N=N bond, which are soluble in water or lower alcohols, particularly nitrosamines, hydrazines, nitramines, azo- and azoxy-compounds, to the corresponding amines; comprising contacting the nitrogen compounds with a hydroxide solution and a nickel-aluminum alloy in the absence of a hydrogen atmosphere, at room temperature and at atmospheric pressure, for a sufficient time to produce the corresponding amine in a single step.

24 Claims, No Drawings

REDUCTIVE DESTRUCTION OF NITROSAMINES, HYDRAZINES, NITRAMINES, AZO- AND AZOXY-COMPOUNDS

This is a continuation of application Ser. No. 282,844, now abandoned filed July 13, 1981.

STATEMENT OF THE INVENTION

This invention relates to an improved method for the destruction of nitrosamines, hydrazines, nitramines, azo- and azoxy-compounds by reduction to the parent amines in a single step using a nickel-aluminum alloy in a base. In the preferred embodiment these compounds are dissolved in solutions of potassium hydroxide and contacted with a nickel-aluminum alloy at room temperature. The process is especially useful for reducing known and potential carcinogens, for example, N-nitrosodimethylamine, to the less toxic amines.

This invention represents an improvement over prior art methods by offering a one-step process effecting the quantitative reduction of these compounds at room temperature, under an air atmosphere, within relatively short reaction times.

BACKGROUND OF THE INVENTION

Nitrosamines, hydrazines, nitramines, azo- and azoxy-compounds are widely used in biological and chemical research. Many of these compounds are potential carcinogens. In particular, N-nitrosodimethylamine (NDMA) is a known carcinogen. A laboratory in which these compounds are being manipulated typically generates potentially carcinogenic refuse in a wide variety of forms, including unused drinking water solutions from animal bioassay experiments, rinsings from distillation apparatus, and aged analytical standards. Because these compounds are known or suspected carcinogens and are found to be generally more toxic than their parent amines, a reliable means for destroying them should be available, including a means to render them innocuous in waste materials prior to disposal. Complete oxidative degradation in an efficient incinerator would seem to be the general approach to destruction of organic carcinogens, but this method can be impractical, especially for large volumes of non-combustible (e.g., aqueous) materials.

Methods for disposing of nitrosamines have been the subject of a substantial amount of experimental inquiry. It has been recommended (Gangolli, Shilling and Lloyd, 1974) that basified aqueous solutions of nitrosamines be degraded by exposing them to aluminum foil; however, we have found (Emmett, Michejda, Sansone and Keefer, 1980) that, while the NDMA is quantitatively consumed by this method, the primary reaction product is N,N-dimethylhydrazine, which is itself a carcinogen in mice.

Photodegradation using ultra violet light has been suggested (Emmett et al, supra) as a method for disposing of NDMA. Experimental results, however, have shown the degradation to be incomplete. In addition, after the removal of the light source, resynthesis reactions are known to take place. Furthermore, the products of photodegradation are also potential carcinogens.

A method which has been recommended (Seebach and Wykypiel, 1979) for the complete reduction of nitrosamines to the less toxic amines is a two-step procedure by which the nitrosamine is first converted to the hydrazine using lithium aluminum hydride in an anhydrous ethereal solvent. The hydrazine is then hydrogenolyzed to the amine in the presence of Raney-nickel under a hydrogen atmosphere. The nitrosamine is first reduced using lithium aluminum hydride, under an inert atmosphere of argon or nitrogen, by refluxing for 3 to 4 hours while heating. The vessel is then placed in an ice bath and an aqueous ammonium solution is added until gas evolution ceases. Thereafter, in a second step, after filtering and washing with hot tetrahydrofuran, the Raney-nickel is added to the solution thus obtained and a hydrogen atmosphere maintained. These reactants are stirred for 10 to 14 hours to effect the conversion to the amine. The conversion is not always quantitative.

We have found a one-step method for the successful quantitative conversion of NDMA to the relatively nontoxic dimethylamine in a variety of solvents commonly used with nitrosamines, including water, mineral oil and dichloromethane, without the hydrogen atmosphere previously used for these and similar reduction processes. This nickel-aluminum-alkali system is a broadly applicable approach to hazard control for work with nitrosamines, hydrazines, nitramines azo- and azoxy-compounds. Although we have found the reduction reaction to progress rapidly, as quantified in the examples below, when treating these materials for disposal we recommend using a reaction time of 24 hours to assure complete conversion to the amine.

This reaction can also be used for the synthesis of amines by the hydrogenation and breaking of N—N or N=N bonds.

DETAILED DESCRIPTION

The following mechanism is hypothesized as that which accomplishes the reductive degradation of the nitrosamines. Wo do not, however, intend to be bound by this hypothesis.

The hydrogenation of nitrogen compounds in basic solution is effected by the nickel-aluminum alloy reacting with the base to oxidize the aluminum and reduce the hydroxy hydrogen to elemental hydrogen. The elemental hydrogen then reacts with the organic in the presence of the nickel catalyst, hydrogenating the organic and cleaving the N—N or N=N bond to form a relatively innocuous product. The reaction with NDMA is believed to occur as follows:

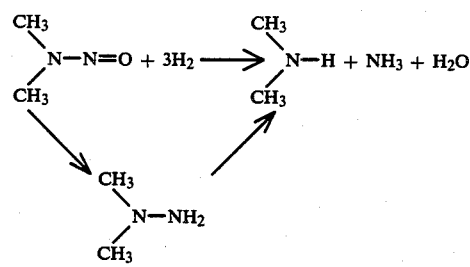

We have found, as in the above equation, N,N-dimethylhydrazine, the carcinogenic product of previously considered degradation reactions for disposing of NDMA by reacting with aluminum alone, is a short-lived intermediate in the present process.

This method can be applied to reduce nitrosamines, hydrazines, nitramines azo and azoxy-compounds of the general formula:

$$\begin{matrix} R_1 \\ \phantom{R_1} \diagdown \\ \phantom{R_1 R_2} \rangle NR_3 \\ \phantom{R_1} \diagup \\ R_2 \end{matrix}$$

$R_1$ and $R_2$ can be hydrogen or any individual organic groups, including ring compounds. $R_1$ and $R_2$ can also be bonded together to form a ring with the nitrogen forming, for example, pyrrolidines, piperidines and morpholines. $R_3$ can be $NH_2$, NHR, RNR, NH, NR, N(O)H, N(O)R, NO, or $NO_2$ where R is an organic group. The limiting requirement for $R_1$, $R_2$ and $R_3$ is that the compound containing the NN be soluble in the reaction medium. Thus, generally, the compound must be at least slightly soluble in water, a hydroxide solution or a lower alcohol. The reduction reaction should progress even for slightly soluble compounds because the compound in solution will be reduced, allowing more compound to be dissolved and subsequently reduced. The reaction will thus progress in the desired direction until reduction is complete.

Compounds which dissolve in a lower alcohol can be reduced by the present method. The lower alcohols are alcohols which are sufficiently soluble in water for the compound dissolved in them to react. They are preferably methanol, ethanol, propanol and isopropanol.

Raney-nickel alloy has been used exclusively as the nickel-aluminum constituent, however, other nickel-aluminum alloys and finely divided mixtures of the two metals, such as mixtures of aluminum and commercially prepared Raney-nickel or sponge nickel, should work as well. It is necessary that the nickel present a very high surface area to the reactants sufficient to catalyze the reduction reaction. The limitation is, therefore, not the particle size of the nickel, but the total surface area.

The process of the present invention is an unexpected improvement over previous methods for the reduction of nitrosamines to their parent amines. Previously, in the two-step process, the reactions were carried out in organic solvents and the second step took place under a hydrogen atmosphere. In the previous one-step reaction, wherein aluminum alone was reacted with a hydroxide, the reaction product was the hydrazine and not the amine. Before discovering the present process, it was thought that insufficient hydrogen would be present to carry through the complete reduction or that the reaction of the aluminum with the hydroxide, generating hydrogen for the reduction reaction, would progress too rapidly to completely reduce the nitrosamine, through the hydrazine intermediate. Surprisingly, in the presence of the nickel, the nitrosamine reduction progressed rapidly enough to reach completion.

We hypothesize that, as the aluminum is oxidized in the nickel-aluminum alloy, sponge nickel is formed. Even after all the aluminum is consumed and hydrogen is no longer being generated, hydrogen adhereing to the surface of the sponge nickel will be present for the reduction to the amine, however, this process was not predictable on the basis of reactions known in the art.

Other metal and metal alloy systems were tested. The results, listed in Table 1, demonstrate the superiority of the present method:

TABLE 1

Reductive Degradation of Nitrosamines ($R_2$—N—N=O)
(Results Expressed as % By Weight In Product $R_2NH/R_2NNH_2$)

| Reactants | $R_2$ is | | |
|---|---|---|---|
| | $(CH_3)_2$ |  | $(C_4H_9)_2$ |
| Ni:Al:KOH | 96/0[a] | 95/0[c] | 99/0[c] |
| Al:KOH | 13/83 | 17/90 | 22/80 |
| Al(Hg) | 88/11 | 82/15 | 66/29 |
| Zn:HCl | 5/85 | 2/101 | 9/85 |
| Cr:HCl | 18/56 | 26/77 | 34/39 |
| TiCl$_3$ | 0[a]/98 | 3/97 | 9/86 |

[a] <1%
[b] <0.5%
[c] <0.1%
Level of detection of nitrosamine, <0.1% (TiCl$_3$ system, 0.5%)

This process differs in several important aspects from the previously known two-step Raney-nickel reduction reaction described above (Seebach and Wykypiel, 1979). The present process requires no first step reduction. Therefore, no lithium aluminum hydride, no heating and no refluxing under an inert atmosphere is required. Nor is ammonia solution addition with cooling, followed by filtering and hot tetrahydrofuran washing necessary between process steps. Furthermore, in what is the second step of the prior art Raney-nickel reduction, Raney-nickel is reacted with the product solution under a hydrogen atmosphere. The present process does not require the separate preparation of Raney-nickel from the Raney-nickel alloy, nor maintenance of a hydrogen atmosphere. The prior art process requires 3 to 4 hours of refluxing in the first step and from 10 to 14 hours of stirring the reactants for the second step to obtain a conversion to the amine, cleaving the N—N bond, sometimes amounting to only about 70%. In contrast, the present process effects a conversion of the nitrosamine greater than 99.9%, any residual nitrosamine or hydrazine being below the level of detection, within 1 to 2 hours of initiating the reaction. Each of nitrosamine and hydrazine is undetectable, less than 0.1%, in the product.

The nickel-aluminum alloy can also be used for the reduction of other nitrosamines, hydrazines, nitramines, azo- and azoxy-compounds to their parent amines. The cleavage of the N—N or N=N bond by hydrogenation has occurred in the presence of nickel for every one of these compounds tested.

The inventors have found specifically that N-nitrosodimethylamine, N-nitrosodiethylamine, N-nitrosodiisopropylamine, N-nitrosodibutylamine, N-nitrosopyrrolidine, N-nitrosopiperidine, N-nitrosomorpholine, N-nitrosomethylphenylamine, N, N'-dinitrosopiperazine, N, N-dimethylhydrazine, N,N-diethylhydrazine, N,N-diisopropylhydrazine, N,N-dibutylhydrazine, N-aminopyrrolidine, N-aminopiperidine, N-aminomorpholine, N-methyl-N-phenylhydrazine, N,N'-diaminopiperazine, N-nitrodiisopropylamine, N-nitromorpholine, phenylhydrazine, p-phenylazoaniline, p-phenylazophenol and 4,4'-azoxyanisole can be reduced to their parent amines by the cleavage of the N—N bond. In all cases the destruction was complete to the limit of detection.

In addition to water solutions of these compounds, the reduction by the present process has been found to be effective in methanol, dichloromethane, mineral oil, olive oil and dimethylsulphoxide solutions. In these cases, aqueous potassium hydroxide solution was added to the reaction mixture, either as a homogeneous mixture or with the reaction taking place in two phases.

EXAMPLE 1

In a typical experiment, 10 μl of NDMA was dissolved in 2 ml of 0.5 M potassium hydroxide solution and treated with 100 mg of Raney-nickel alloy (Alfa Div., Ventron Corp.). They were initially at room temperature. There was some increase in temperature due to heat of reaction.

Aliquots of 0.5 μl each were analyzed at various times during the course of reaction by direct injection into a Hewlett Packard 5830A Gas Chromatograph equipped with a 2 mm inner diameter glass column, 1.83 m long, packed with 10% Carbowax 20M plus 2% potassium hydroxide on Chromosorb WAW. Column temperature was maintained at 50°, and the nitrogen flow rate was constant at 19 ml/min. The flame ionization detector peaks were automatically quantitated by the instrument's integrator unit, and the integrals for each peak were compared with those of independently prepared standard solutions. Retention times for the standard peaks were 0.6 min. for dimethylamine, 1.4 min. for N,N-dimethylhydrazine, and 17 min. for NDMA under these conditions.

When reduction was complete, the resulting slurry was suction filtered through Celite taking care not to let the potentially pyrophoric filter cake dry in the presence of organic solvents or other flammable materials. The spent nickel was preferably recycled, or else carefully discarded with the solid waste after autoxidation was demonstrably complete. It may also be cautiously dissolved in mineral acid for disposal.

Destruction of NDMA was very rapid ($t_{\frac{1}{2}} \sim 2$ min.) in the typical reaction mixture. N,N-dimethylhydrazine was observed as an intermediate but was destroyed as the reduction progressed. The final reaction mixture, analyzed after 1–2 hours, showed only dimethylamine, with no trace of N,N-dimethylhydrazine or NDMA. The detection limit was 0.1% for the nitrosamine and 1% for the hydrazine.

EXAMPLE 2

N,N-dimethylhydrazine was used in place of the NDMA and reacted using the procedure described in Example 1.

The N,N-dimethylhydrazine was converted rapidly ($t_{\frac{1}{2}} \sim 4$ min.) and quantitatively to dimethylamine within the limits of detection.

COMPARATIVE EXAMPLE 1

The procedure of Example 1 was followed using 11 mg of aluminum foil in place of the nickel-aluminum alloy. Dimethylamine was obtained as the minor product (13%) and N,N-dimethylhydrazine as the major product (83%).

EXAMPLE 3

The procedure of Example 1 was followed with the aqueous solvent being replaced by the following:

(a) Methanol: 1 M potassium hydroxide was used in the volume ratio of 90:10. The NDMA was again quantitatively reduced to dimethylamine, but at a slower rate ($t_{\frac{1}{2}} \sim 60$ min.).

(b) Dichloromethane: 1 M potassium hydroxide: methanol were used in the volume ratios 20:20:60. The destruction of the NDMA was also rather slow ($t_{\frac{1}{2}} \sim 35$ min.), but quantitatively complete.

(c) Mineral oil: hexane: 1 M potassium hydroxide were used in the volume ratios of 25:25:50. An aqueous oil two phase system was maintained during the procedure. Reduction appeared to take place as rapidly as in the original aqueous medium ($t_{\frac{1}{2}} \sim 2$ min.).

Tables 2 and 3, which follow, recite the results of reducing various nitrosamines, hydrazines and nitramines using the present method:

TABLE 2

Reductive Degradation of Nitrosamines ($R_2NNO$) Using a Nickel-Aluminum Alloy in Potassium Hydroxide Solution
(Results Expressed As % By Weight In Product)

| $R_2$ | $R_2NH$ | $R_2NNH_2$ | $R_2NNO$ |
|---|---|---|---|
| Dimethyl | 96 | <1 | <0.1 |
| Diethyl | 92 | <0.1 | <0.1 |
| Di-isopropyl | 96 | <0.1 | <0.1 |
| Di-n-butyl | 99 | <0.1 | <0.1 |
| Pyrrolidine | 95 | <0.1 | <0.1 |
| Piperidine | 94 | <0.1 | <0.1 |
| Morpholine | 97 | <0.1 | <0.1 |
| Methylphenyl | 100* | <0.5 | <0.1 |
| Piperazine | 88 | <1 | <0.5 |

*complete within the error of detection

TABLE 3

Reductive Degradation of Hydrazines ($R_2NNH_2$) And Nitramines ($R_2NNO_2$) Using A Nickel-Aluminum Alloy In Potassium Hydroxide Solution
(Results Expressed As % By Weight In Product)

| | $R_2NH$ | $R_2NNH_2$ | $R_2NNO$ | $R_2NNO_2$ |
|---|---|---|---|---|
| $(CH_3)_2NNH_2$ | 97 | <1 | — | — |
| $(C_2H_5)_2NNH_2$ | 100* | <0.1 | — | — |
| $(i-C_3H_7)_2NNH_2$ | 100* | <0.1 | — | — |
| $(n-C_4H_9)_2NNH_2$ | 93 | <0.1 | — | — |
| 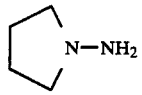 | 100* | <0.25 | — | — |
| 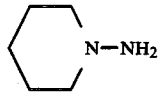 | 89 | <.1 | — | — |
| 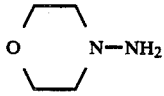 | 100* | <0.1 | — | — |
| $(CH_3)(C_6H_5)N-NH_2$ | 96 | <0.05 | — | — |
| $(i-C_3H_7)_2N-NO_2$ | 100* | <0.1 | <0.1 | <0.1 |
| 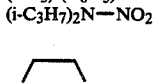 | 92 | <0.1 | <0.1 | <0.1 |
| $C_6H_5NHNH_2$ | 98 | <0.2 | — | — |
| 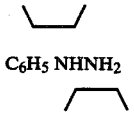 | 73 | <1 | — | — |

*complete within the error of detection

We have demonstrated with the present invention the process of breaking the N—N or N=N bond by catalytic hydrogenation using the nickel-aluminum alloy in a basic solution. This is particularly useful in degrading known and suspected carcinogens in the nitrosamine, hydrazine, nitramine, azo- and azoxy-compound families. This process can be used for rendering less toxic laboratory and industrial process wastes and by-products which heretofore have presented both hazardous and costly disposal problems.

This invention is intended to include the use of the nickel-aluminum alloy in the base reduction process, within the limits of the claims, for by-product and waste disposal applications as well as synthesis reactions. The examples and tables included above are offered to demonstrate this invention, but not to limit its scope.

We claim:

1. A single stage process for reducing the toxicity and the carcinogenic potential of the class of suspected carcinogenic compounds characterized by having at least two nitrogens bonded together within the molecule by conversion to the corresponding amine which comprises reducing said compounds with a nickel-aluminum alloy in a hydroxide solution in the absence of a hydrogen atmosphere, at room temperature and at atmospheric pressure, whereby destruction of the nitrogen-nitrogen bond is greater than 99% complete.

2. A single step process for the quantitative reduction of nitrogen compounds, which are soluble in water or lower alcohols and which contain a N—N or N═N bond, to the corresponding amines, which comprises reacting the nitrogen compounds in a hydroxide solution with a nickel-aluminum alloy, in the absence of a hydrogen atmosphere, at room temperature and at atmospheric pressure, for a sufficient time to produce the corresponding amines.

3. A process as recited in claim 2, for the reduction of nitrogen compounds which are soluble in water or a lower alcohol selected from the group consisting of nitrosamines, hydrazines, nitramines, azo- and azoxy-compounds to the corresponding amines, which comprises contacting the nitrogen compounds with a hydroxide solution and a nickel-aluminum alloy for a sufficient time to produce the corresponding amine in a single step.

4. A process for the reduction of nitrogen compounds as recited in claim 3, wherein the nitrogen compounds are of the formula $R_1R_2NR_3$, and $R_1$ and $R_2$ are hydrogen, alkyl groups of 1 to 6 carbon atoms, aromatic groups, or groups of 1 to 6 carbon atoms containing in addition nitrogen or oxygen atoms, and $R_3$ is NH, $NH_2$, NO, $NO_2$ or N(O)H.

5. A process as recited in claim 4, wherein $R_1$ and $R_2$ are identical and are alkyl groups.

6. A process as recited in claim 4, wherein $R_1$ and $R_2$ are bonded together to form cyclic organic functional groups chosen from the group consisting of pyrrolidines, piperidines, and morpholines.

7. A process as recited in claim 4, wherein $R_1$ is methyl and $R_2$ is phenyl.

8. A process as recited in claim 4, wherein $R_1$ and $R_2$ are hydrogen, methyl, ethyl, isopropyl or butyl, and wherein $R_1$ and $R_2$ are identical.

9. A process as recited in claim 3, wherein the nitrogen compound is N-nitrosodiumethylamine, N-nitrosodiethylamine, N-nitrosodiisopropylamine, N-nitrosodibutylamine, N-nitrosopyrrolidine, N-nitrosopiperidine, N-nitrosomorpholine, N-nitrosomethylphenylamine, N,N'-dinitrosopiperazine, N,N-dimethylhydrazine, N,N-diethylhydrazine, N,N-diisopropylhydrazine, N,N-dibutylhydrazine, N-aminopyrrolidine, N-aminopiperidine, N-aminomorpholine, N,N'-diaminopiperazine, N-methyl-N-phenylhydrazine, N-nitrodiisopropylamine, N-nitromorpholine, phenylhydrazine, p-phenylazoaniline, p-phenylazophenol, or 4,4'-azoxyanisole.

10. A process as recited in claim 2, wherein N-nitrosodimethylamine is reduced to the corresponding amine.

11. A process as recited in claim 1, wherein the suspected carcinogenic compounds are N-nitrosodimethylamine, N-nitrosodiethylamine, N-nitrosodiisopropylamine, N-nitrosodibutylamine, N-nitrosopyrrolidine, N-nitrosopiperidine, N-nitrosomorpholine, N-nitrosomethylphenylamine, N,N'-dinitrosopiperazine, N,N-dimethylhydrazine, N,N-diethylhydrazine, N,N-diisopropylhydrazine, N,N-dibutylhydrazine, N-aminopyrrolidine, N-aminopiperidine, N-aminomorpholine, N-methyl-N-phenylhydrazine, N,N'-diaminopiperazine, N-nitrodiisopropylamine, N-nitromorpholine, phenylhydrazine, p-phenylazoaniline, p-phenylazophenol and 4,4'-azoxyanisole.

12. A process as recited in claim 4 wherein $R_3$ is $NR_1R_2$, NR, or N(O)R, and $R_1$ and $R_2$ are hydrogen, alkyl groups of 1 to 6 carbon atoms, aromatic groups, or groups of 1 to 6 carbon atoms containing in addition nitrogen or oxygen atoms.

13. The process as recited in claim 2, wherein a nitrosamine is reduced to the corresponding amine.

14. The process as recited in claim 2, wherein a hydrazine is reduced to the corresponding amine.

15. The process as recited in claim 2, wherein a nitramine is reduced to the corresponding amine.

16. The process as recited in claim 2, wherein an azo-compound is reduced to the corresponding amine.

17. The process as recited in claim 2, wherein an azoxy-compound is reduced to the corresponding amine.

18. A process for the reduction of nitrogen compounds as recited in claim 13, wherein the nitrogen compounds are of the formula $R_1R_2NR_3$, and $R_1$ and $R_2$ are hydrogen, alkyl groups of 1 to 6 carbon atoms, aromatic groups, groups of 1 to 6 carbon atoms containing in addition nitrogen or oxygen atoms, or are organic groups bonded together to form cyclic organic functional groups, and $R_3$ is NO.

19. A process as recited in claim 13, wherein the nitrosamine is chosen from the group consisting of N-nitrosodimethylamine, N-nitrosodiethylamine, N-nitrosodiisopropylamine, N-nitrosodibutylamine, N-nitrosopyrrolidine, N-nitrosopiperidine, N-nitrosomorpholine, N-nitrosomethylphenylamine and N,N'-dinitrosopiperazine.

20. A single stage process for reducing the toxicity and the carcinogenic potential of the class of suspected carcinogenic compounds as recited in claim 1, wherein the reaction takes place in an open vessel at room temperature.

21. A process as recited in claim 1, wherein the nickel-aluminum alloy is Raney-nickel alloy.

22. A process as recited in claim 2, wherein the nickel-aluminum is Raney-nickel alloy.

23. A process as recited in claim 1, wherein the nickel-aluminum alloy is replaced by a mixture of aluminum and nickel particles, the nickel particles presenting a very high surface area sufficient to catalyze the reduction reaction.

24. A process as recited in claim 2, wherein the nickel-aluminum alloy is replaced by a mixture of aluminum and nickel particles, the nickel particles presenting a very high surface area sufficient to catalyze the reduction reaction.

* * * * *